(12) United States Patent
Chen (10) Patent No.: US 6,599,270 B1
(45) Date of Patent: Jul. 29, 2003

(54) SYRINGE WITH A SNAPPING DEVICE FOR BACKWARD PULLING THE NEEDLE INTO THE SYRINGE AFTER SYRINGING

(76) Inventor: Cho Ying Chen, P.O. Box 2103, Taichung (TW)

( * ) Notice: Subject to any disclaimer, the term of this patent is extended or adjusted under 35 U.S.C. 154(b) by 0 days.

(21) Appl. No.: 10/282,301

(22) Filed: Oct. 29, 2002

(51) Int. Cl.[7] .................................. A61M 5/00
(52) U.S. Cl. ........................................ 604/110
(58) Field of Search ..................... 604/110, 192, 604/195, 198, 163, 263, 187, 171

(56) References Cited

U.S. PATENT DOCUMENTS

| | | | | | |
|---|---|---|---|---|---|
| 4,927,414 | A | * | 5/1990 | Kulli ........................... | 604/110 |
| 4,957,490 | A | * | 9/1990 | Byrne et al. ................ | 604/197 |
| 5,401,246 | A | * | 3/1995 | Mazur et al. ............... | 604/110 |
| 6,077,253 | A | * | 6/2000 | Cosme ........................ | 604/263 |
| 6,149,630 | A | * | 11/2000 | Robinson .................... | 604/198 |
| 6,183,440 | B1 | * | 2/2001 | Bell ........................... | 604/110 |
| 6,461,362 | B1 | * | 10/2002 | Halseth et al. .............. | 606/108 |

* cited by examiner

*Primary Examiner*—Sharon Kennedy (57) ABSTRACT

A syringe includes a hollow barrel and a plunger partially and movably received in the hollow barrel. A connector centrally extends toward the first end of the hollow barrel from the plunger. A snapping device includes a body slidably received in the hollow barrel and selectively engaged to the connector. Two locking member downward extend from the annular protrusion. Each locking member has a first hook formed on a middle portion and extending toward the inner periphery of the hollow barrel to engage to the hollow barrel. A hollow stub extends from the body. An annular slit is defined in the hollow stub. A second hook extends from the locking member and is selectively engaged to the annular slit. A pusher extends through the hollow barrel such that the first hook is detached from the hollow barrel when the pusher is inward compressed.

9 Claims, 13 Drawing Sheets

SYRINGE WITH A SNAPPING DEVICE FOR BACKWARD PULLING THE NEEDLE INTO THE SYRINGE AFTER SYRINGING

BACKGROUND OF THE INVENTION

1. Field of the Invention

The present invention relates to a syringe, and more particularly to syringe with a snapping device for backward pulling the needle into syringe after syringing.

2. Description of Related Art

Figure 16:
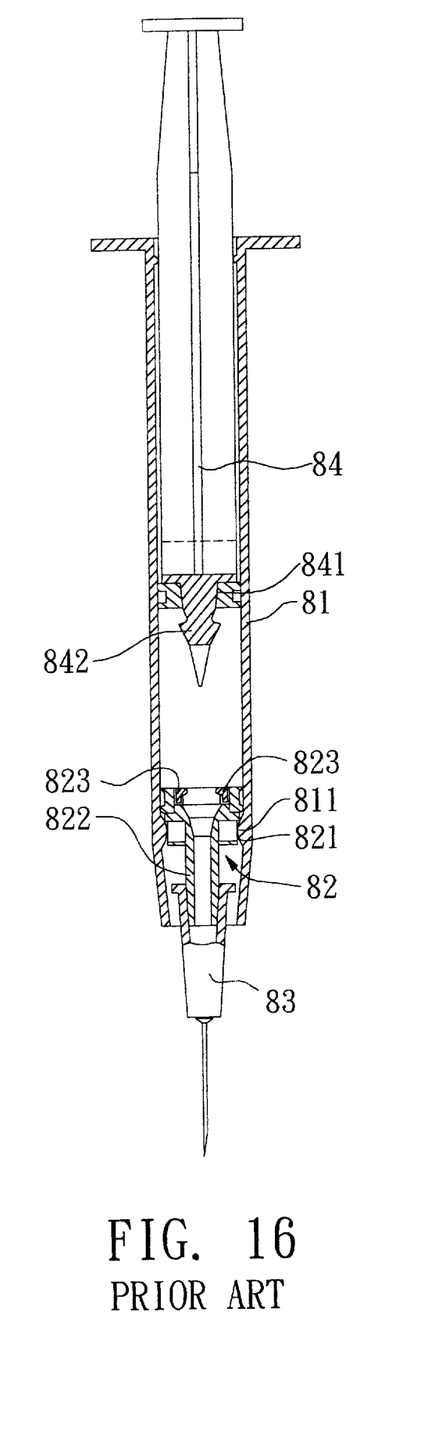
FIG. 16 is a side cross-sectional view of a syringe with a snapping device for backward pulling the needle into the syringe after syringing in accordance with the prior art.
Figure 17:
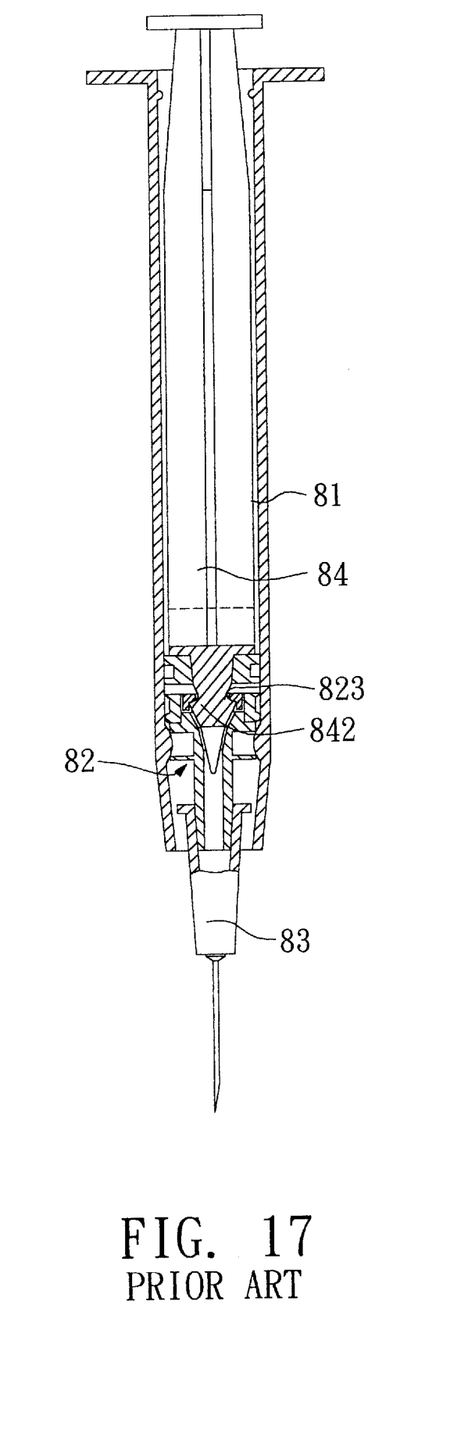
FIG. 17 is an operational cross-sectional view of the syringe in FIG. 16 when the plunger is connected to the snapping device of the syringe in FIG. 16.

A conventional syringe in accordance with the prior art shown in FIGS. 16 and 17 comprises a hollow barrel (81), a snapping device (82) secured in a first end of the hollow barrel (81), a needle hub (83) securely connected to the snapping device (82) and extending through the hollow barrel (81) and the plunger (84) movably received in the hollow barrel (81).

The hollow barrel (81) includes an annular protrusion (811) extending from the inner periphery of the hollow barrel (81). The snapping device (82) includes a body (not numbered) having a through hole (not numbered) centrically defined in the body. A concave (821) is defined in the outer periphery of the body to partially receive the protrusion (811) of the hollow barrel (81). A hollow stub (822) centrically extends from the body toward the first end of the hollow barrel (81). The needle hub (83) is securely connected to the hollow stub (822). The snapping device (82) includes an annular hook (823) from on an inner periphery of the through hole in the body of the snapping device opposite to the needle hub (83).

The plunger (84) includes a first end movably received in the hollow barrel (81) and a bulb (841) attached to the first end of the plunger (84). The bulb (841) abuts the inner periphery of the hollow barrel (81). An arrow (842) centrically extends from the bulb (841) toward the snapping device (82).

When finishing syringing, the arrow (842) is inserted into the through hole in the body of the snapping device (82) and engaged to the hook (823) to form a connection stronger than that between the annular protrusion (811) and the concave (821). Consequently, the snapping device (82) and the needle hub with the needle are pulled into the hollow barrel (81) to prevent the medical workers from being pricked and accidentally infected by the used needle when the plunger (84) is backward pulled after syringing.

However, the snapping device (82) is connected to the hollow barrel (81) only by the protrusion (811) being received in the concave (821) in the snapping device (82). Consequently, the snapping device (82) is securely connected to the hollow barrel (81) when the protrusion (811) has a height greater than a depth of the concave (821) to prevent the snapping device (82) from falling into the hollow barrel (81) when mounting the needle hub (83) onto the hollow stub (822) of the snapping device (82). However, the plunger (84) cannot backward pull the snapping device (82) and the needle hub (83) into the hollow barrel (81) after syringing when the connection between the snapping device (82) and the hollow barrel (81) is greater than that between the snapping device (82) and the arrow (842) of the plunger (84) such that the needle will expose out of the hollow barrel (81) and hurt the medical workers. On the contrary, the connector will fall into the hollow barrel (81) when attaching the needle (83) to the snapping device (82).

The present invention has arisen to mitigate and/or obviate the disadvantages of the conventional syringe with a snapping device.

SUMMARY OF THE INVENTION

The main objective of the present invention is to provide an improved syringe with a snapping device for backward pulling the needle into the syringe after syringing to prevent the medical workers from being pricked and accidentally infected by the used needle.

To achieve the objective, the syringe in accordance with the present invention comprises a hollow barrel and a plunger partially and movably received in the hollow barrel. A connector centrally extends toward the first end of the hollow barrel from the plunger. A snapping device includes a body slidably received in the hollow barrel and selectively engaged to the connector. Two locking member downward extend from the annular protrusion. Each locking member has a first hook formed on a middle portion and extending toward the inner periphery of the hollow barrel to engage to the hollow barrel. A hollow stub extends from the body. An annular slit is defined in the hollow stub. A second hook extends from the locking member and is selectively engaged to the annular slit. A pusher extends through the hollow barrel such that the first hook is detached from the hollow barrel when the pusher is inward compressed.

Further benefits and advantages of the present invention will become apparent after a careful reading of the detailed description with appropriate reference to the accompanying drawings.

DETAILED DESCRIPTION OF THE INVENTION

Referring to the drawings and initially to FIGS. 1–9, it is a first embodiment of a syringe in accordance with the present invention. The syringe has a snapping device for backward pulling the needle into the syringe after syringing.

Figure 1:
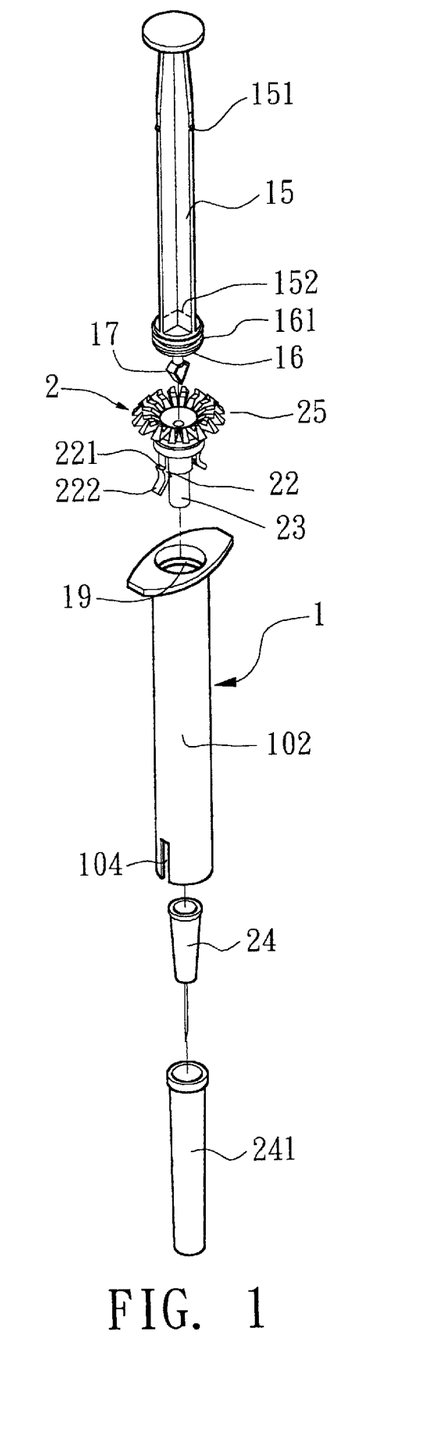
FIG. 1 is a perspective view of a syringe with a snapping device for backward pulling the needle into the syringe after syringing in accordance with the present invention.
Figure 2:
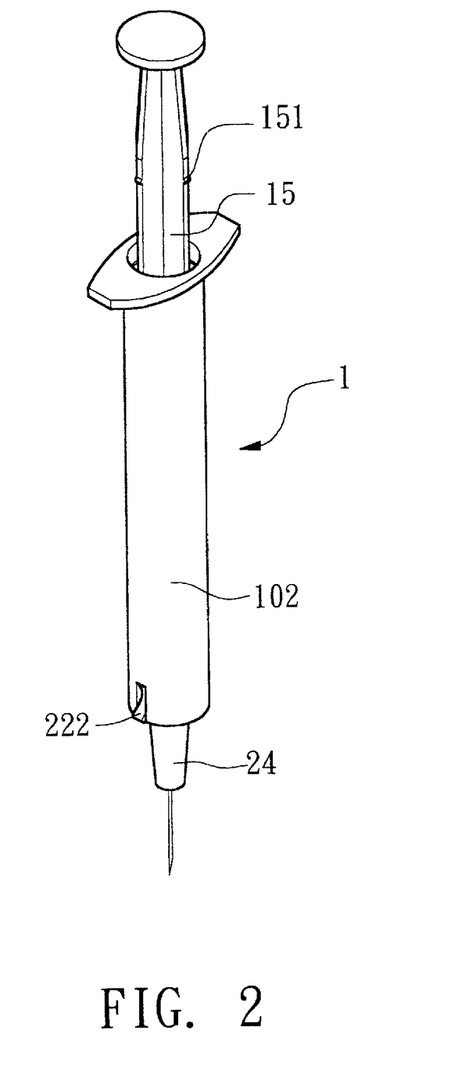
FIG. 2 is an exploded perspective view of the syringe in FIG. 1.
Figure 3:
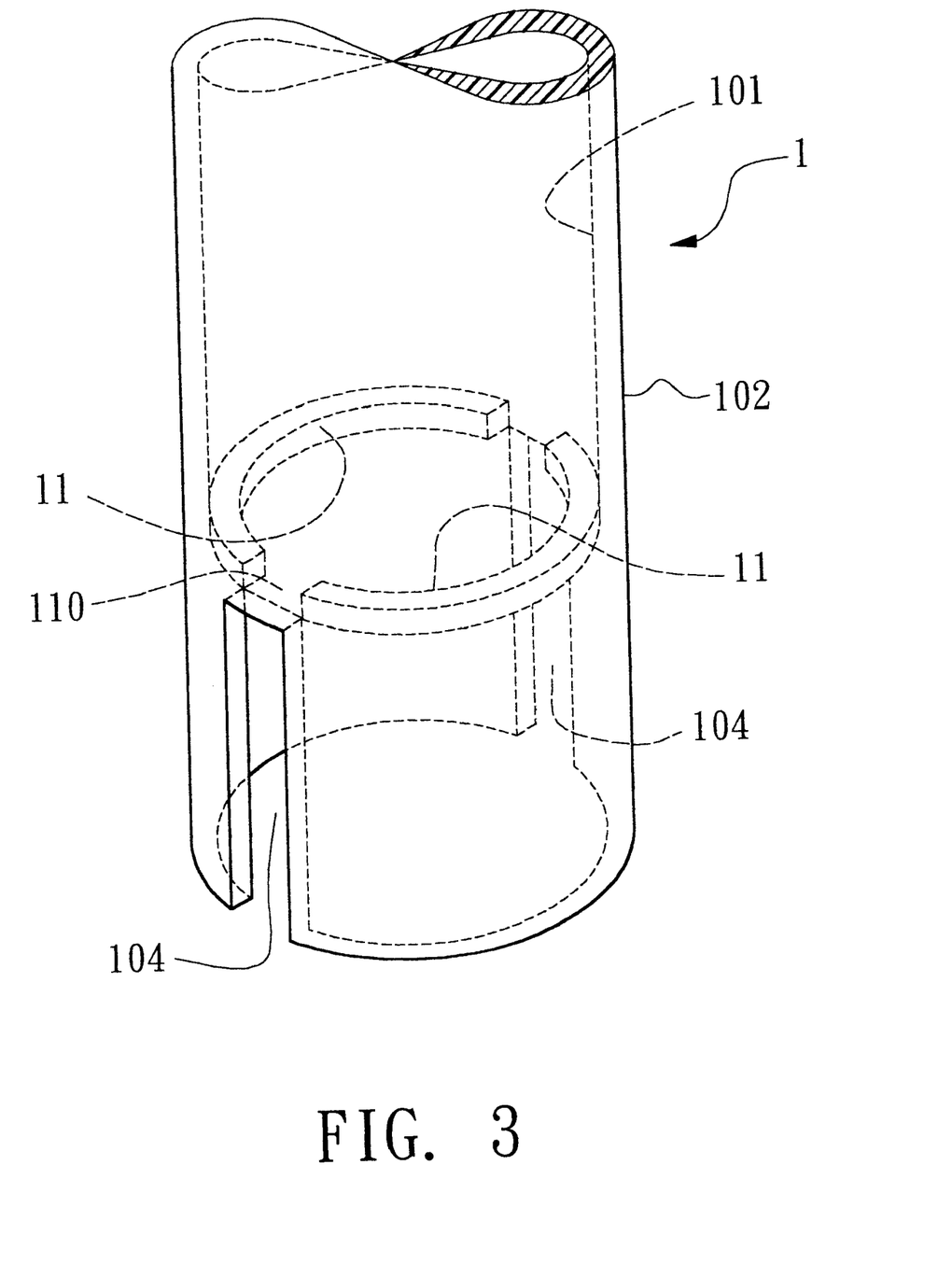
FIG. 3 is a partial perspective view of the hollow barrel of the present invention in FIG. 1.

With reference to FIGS. 1–3, the syringe comprises a hollow barrel (1) having an inner periphery (101), an outer periphery (102) and a first end (103). Two flanges (11) extend from the inner periphery of the hollow barrel (101) near the first end (103) of the hollow barrel (1) and each has a cubic section. The two flanges (11) diametrically correspond to each other and formed two gaps (110) between the two flanges (11). The two gaps (110) diametrically correspond to each other. Two slots (104) are longitudinally defined in the first end (103) of the hollow barrel (1) and diametrically correspond to each other. Each slot (104) aligns with a corresponding one of the two gaps (110) and communicates with the inner periphery (101) and the outer periphery (102) of the hollow barrel (1). An annular protrusion (19) extends from the inner periphery (101) of the hollow barrel (1) opposite to the first end (103) of the hollow barrel (1).

Figure 5:
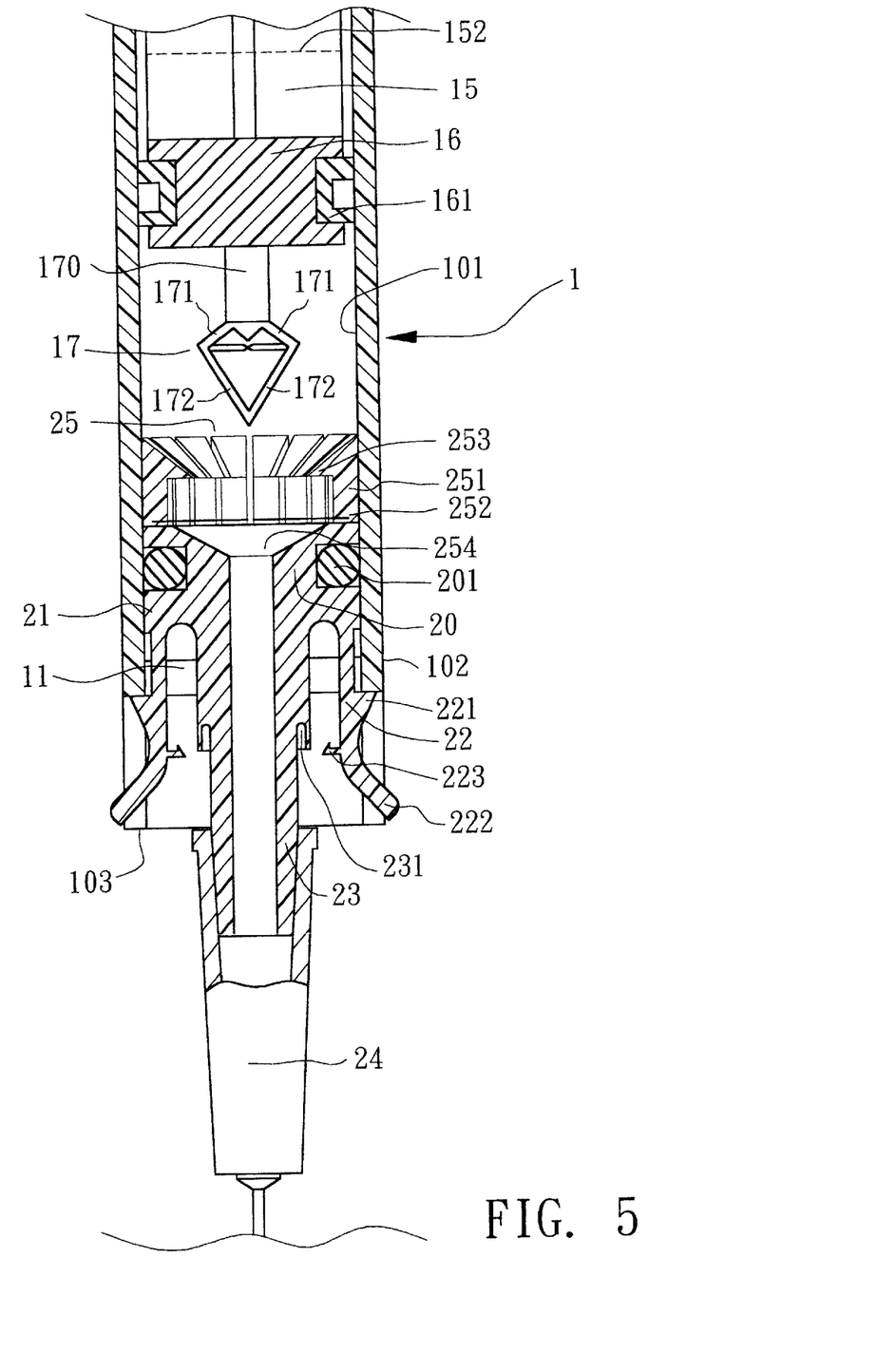
FIG. 5 is partially cross-sectional side plan view of the syringe of the present invention in FIG. 1.
Figure 6:
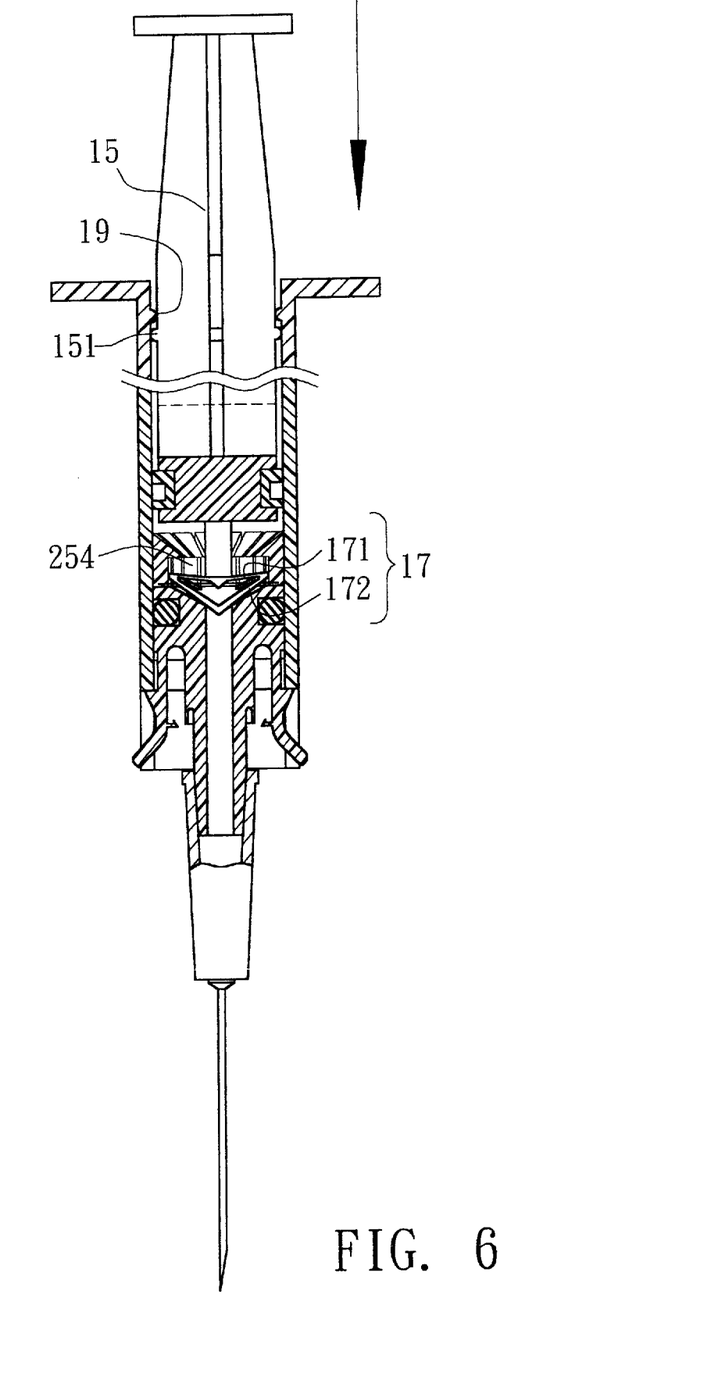
FIG. 6 is a cross-sectional side plan view of the syringe of the present invention when the plunger is connected to the snapping device.

Further with reference to FIG. 5, a plunger (15) is partially and movably received in the hollow barrel (1). The plunger (15) includes a front end (16) toward the first end (103) of the hollow barrel (1) and having a first rubber bulb (161) mounted around the front end (16) of the plunger (15). The plunger (15) includes a notch (152) defined therein near the front end (16) of the plunger (15) and multiple bosses (151) formed on a periphery of the plunger (15). A connector (17) centrally extends from the front end of the plunger (15) toward the first end (103) of the hollow barrel (1). The connector (17) includes a shaft (170) centrally and perpendicularly extending from the front end (16) of plunger (15). The connector (17) includes two wing plates (171) obliquely extending from a free end of the shaft (170) toward the inner periphery of the hollow barrel (1) and two resilient plates (172) respectively extending from a corresponding one of the free ends of the two wing plates (171). The free ends of the two resilient plates (172) are connected to each other such that the two wing plates (171) and the two resilient plates (172) form a rhombus.

Figure 4:
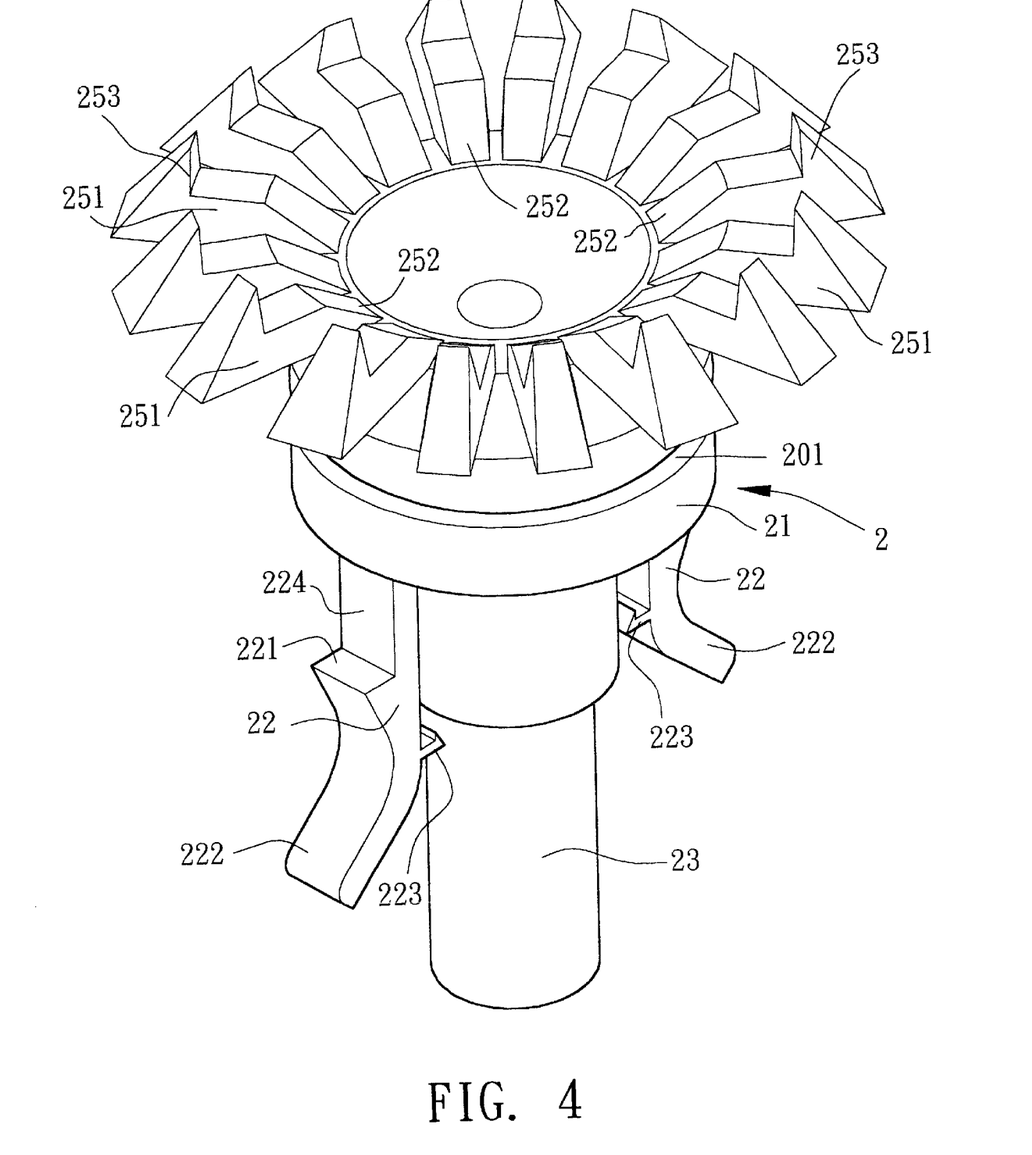
FIG. 4 is a perspective view of the snapping device of the present invention in FIG. 1.

With reference to FIGS. 4 and 5, a snapping device (2) is slidably received in the hollow barrel (1). The snapping device (2) includes a body (20) slidably received in the hollow barrel (1) and selectively being engaged to the connector (17), and a second rubber bulb (201) mounted around the body (20). The second rubber bulb (201) abuts the inner periphery of the hollow barrel (1). An annular protrusion (21) extends from an outer periphery of the body (20) of the snapping device (2) and two locking members (22) downward extend from the annular protrusion (21) of the snapping device (2). The two locking members (22) diametrically correspond to each other and respectively align with a corresponding one of the gaps (110) of the hollow barrel (1). Each locking member (22) includes a first hook (221) formed on a middle portion of the locking member (22) and extending toward the inner periphery of the hollow barrel (1) such that a recess (224) is formed between the first hook (221) and the annular protrusion (21), a second hook (223) formed opposite to the first hook (221) toward an axis of the body (20) and a pusher (222) extending opposite to each other. A distance between free ends of the two pushers (222) is greater than a diameter of the hollow barrel (1) so that the two pushers (222) extend through the hollow barrel (1) via the slots (104) in the hollow barrel (1) when the first hook (221) is engaged to the top of the slot (104) and the flange (11) of the hollow barrel (1) is received in the recess (224) to hold the snapping device (2) in place. A hollow stub (23) centrally and longitudinally extends from the body (20) and a needle hub (24) is attached to the hollow stub (23). The hollow stub (23) has an annular slit (231) defined therein the second hook (223) is engaged to the slit (231) when the two pusher (222) is inward compressed.

A connecting portion (25) is formed on a top of the body (20). The connecting portion (25) includes multiple claws (251) each radially extending from the top of the body (20). The claw (251) includes a resilient portion (252) connecting to the body (20) and a hook (253) formed on a free end of the claw (251). A concavity (254) is centrally defined in the top of the body (20) within the claws (251). Further with reference to FIG. 7, the two wing plates (171) of the connector (17) extend to engaged to the hooks (253) when the resilient plates (172) abut the bottom of the concavity (254) such that the snapping device (2) is securely connected to the plunger (15) and can be driven by the plunger (15) after compressing the pushes (222). However, the bosses (151) and the annular protrusion (19) of the hollow barrel (1) can prevent the plunger (15) from being connected to the snapping device (2) before finishing syringing.

Figure 7:
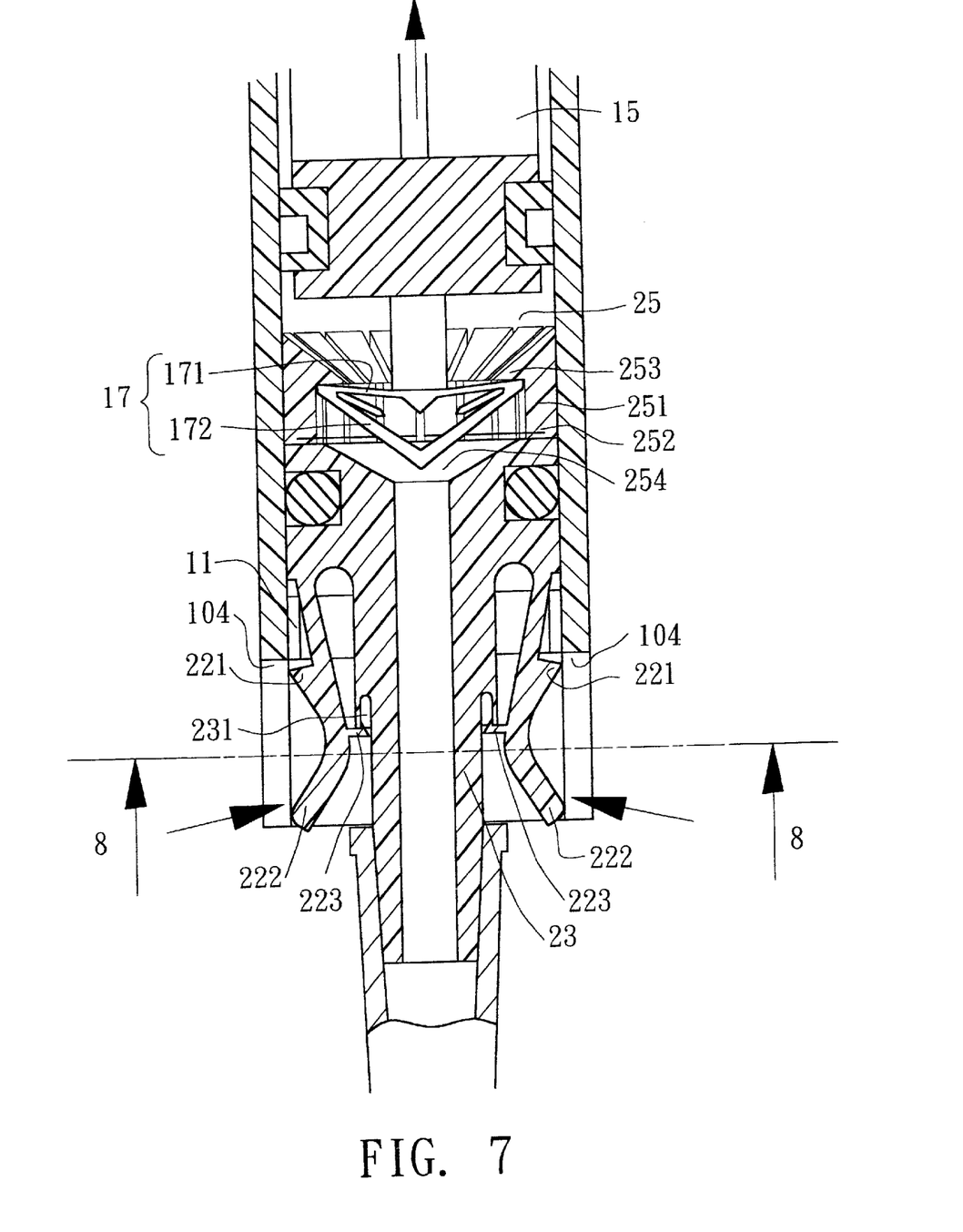
FIG. 7 is a partially cross-sectional side plan view of the syringe of the present invention when the plunger is backward moved to pull the needle with the needle into hollow barrel.
Figure 8:
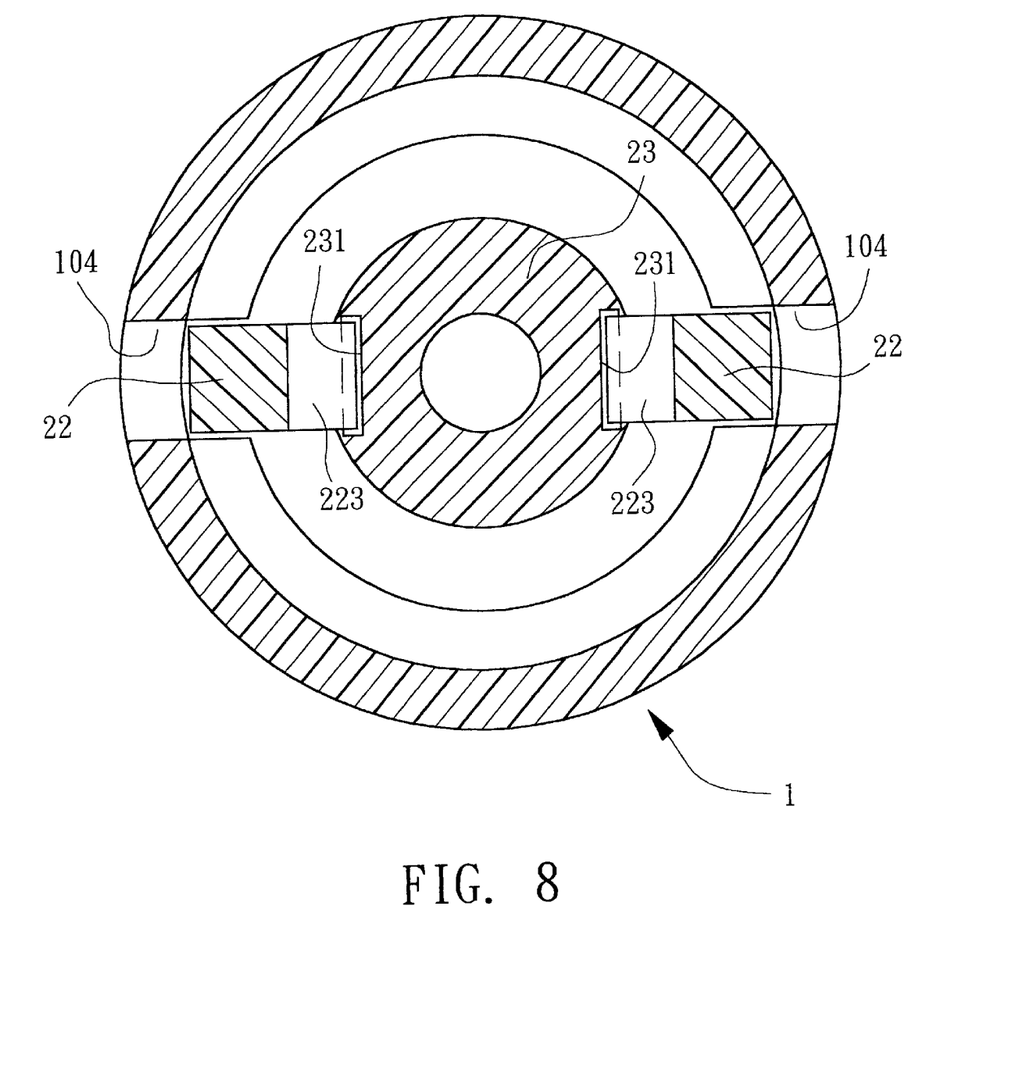
FIG. 8 is a top cross-sectional view of the syringe along line 8—8 in FIG. 7.
Figure 9:
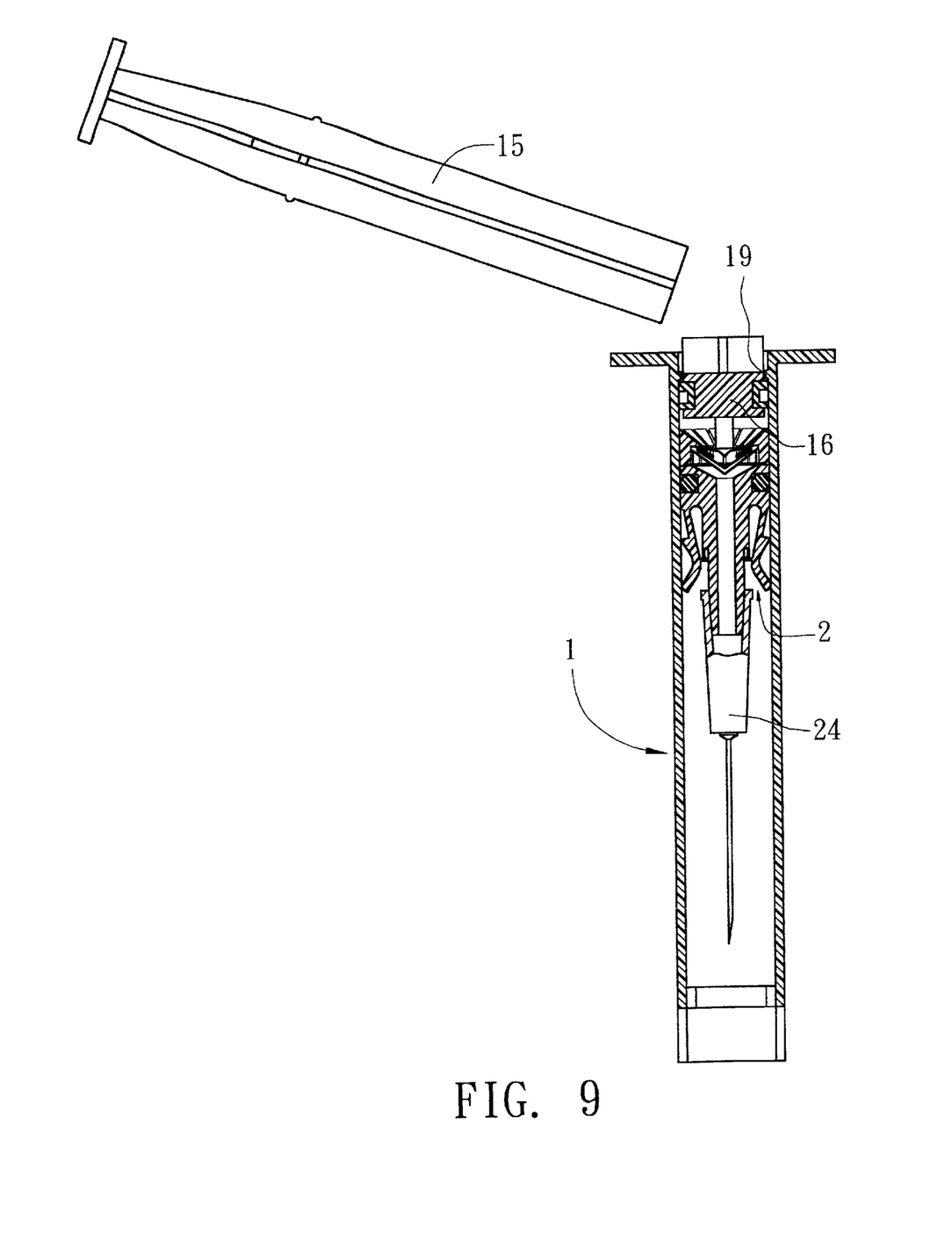
FIG. 9 is an operational plan view in cross-section when the needle has been pulled into the hollow barrel.

When finishing syringing, the bosses (151) abut the annular protrusion (19) of the hollow barrel (1). With reference to FIGS. 7 and 8, the connector (17) stretches to engaged to the hooks (253) when the user continually downward pushes the plunger (15) to make the resilient plates (172) abutting the bottom of the concavity (254) and then the snapping device (2) with the needle hub (24) can be backward pulled into the hollow barrel (1) after inward compressing the pusher (222) to make the first hook (221) detaching from the bottom of the slot (104) in the hollow barrel (1) and the second hook (223) engaging to the slit (231). The plunger (15) is divided into two pieces from the notch (152) when the snapping device (2) and the needle hub (24) with the needle are fully received in the hollow barrel (1).

Figure 10:
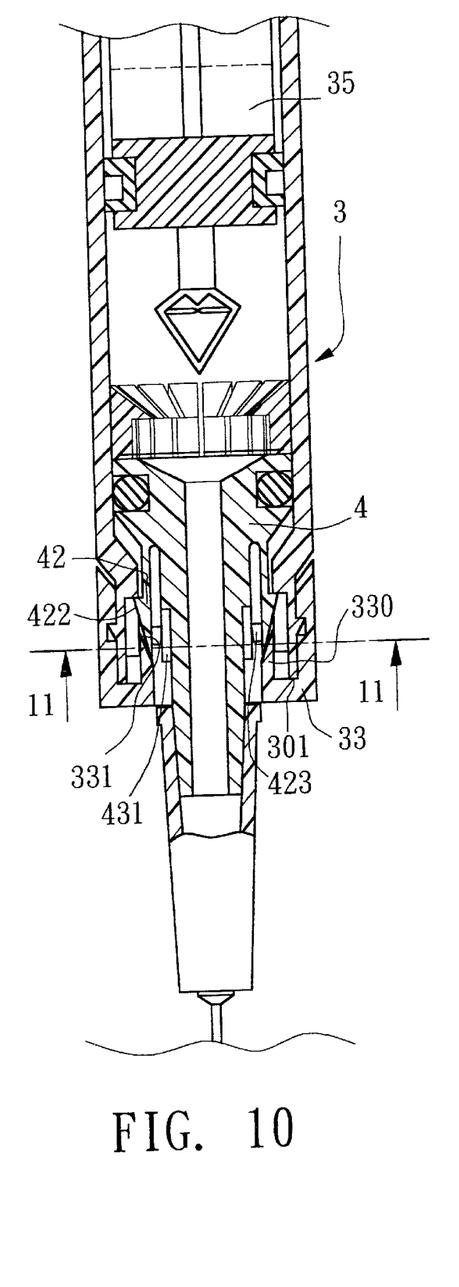
FIG. 10 is a side cross-sectional view of a second embodiment of the syringe in accordance with the present invention.
Figure 11:
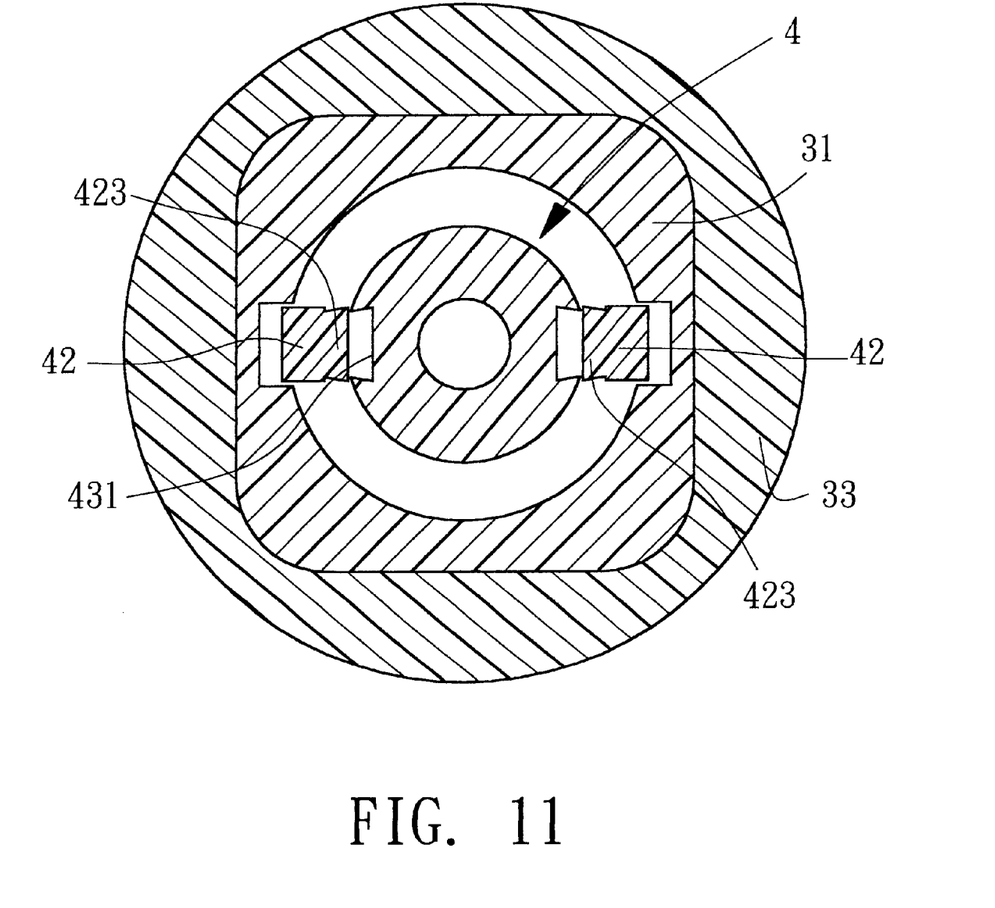
FIG. 11 is a bottom plan view in cross-section of the syringe in FIG. 10 along line 11—11.
Figure 12:
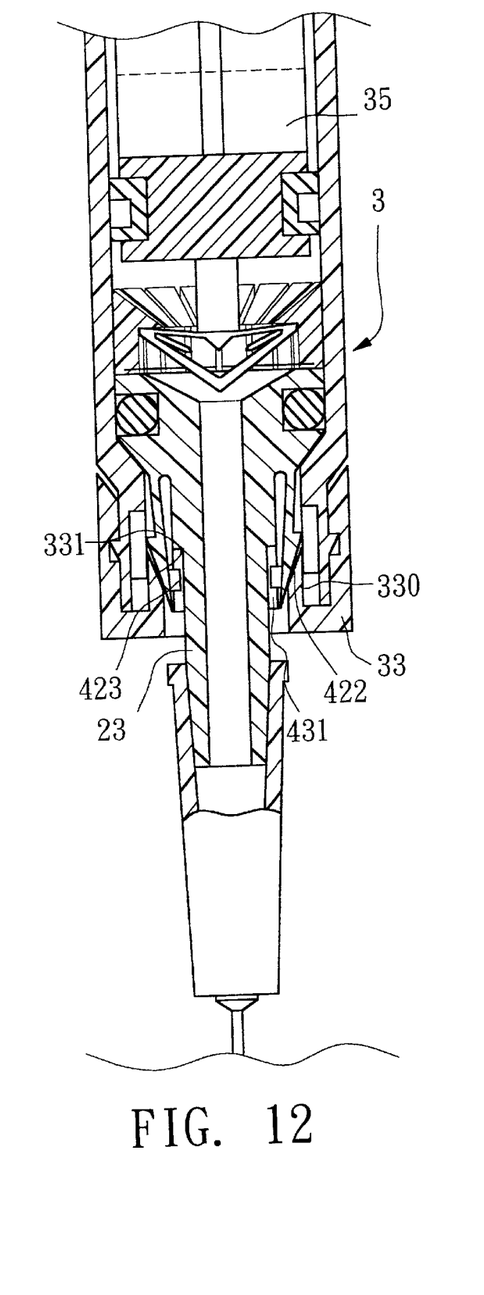
FIG. 12 is an operational side cross-sectional view of the syringe of the present invention in FIG. 10.

With reference to FIGS. 10–12, it is a second embodiment of the syringe in accordance with the present invention. Each locking member (42) includes a dovetail flange (423) extending from the locking member (42) toward the needle hub (23) and a guiding side (422) formed opposite to the dovetail flange (423) under the first hook of the locking member (42). Two dovetail grooves (431) are diametrically defined in the needle hub (23) and each aligns with a corresponding one of the two dovetail flanges (423). An end cap (33) is attached to the first end (301) of the hollow barrel (3). Two stubs (330) upwardly extend from a bottom of the end cap (33) and each aligns with a corresponding one of the two locking member (42). A guiding side (331) is formed on a free end of each of the two stubs (330) and aligns with a corresponding one of the two guiding sides (422) of the locking member (42). The locking member (42) is inward moved to make the dovetail flange (423) secured in the dovetail groove (431) when the plunger (35) is downward moved and the bosses (151) moved over the annular protrusion (19). The locking member (42) will not move to the original position after the dovetail flange (423) is securely received in the dovetail groove (431) such that the snapping device (4) is detached from the hollow barrel (3) and can be pulled into the hollow barrel (3) to achieve the objective of the present invention.

Figure 13:
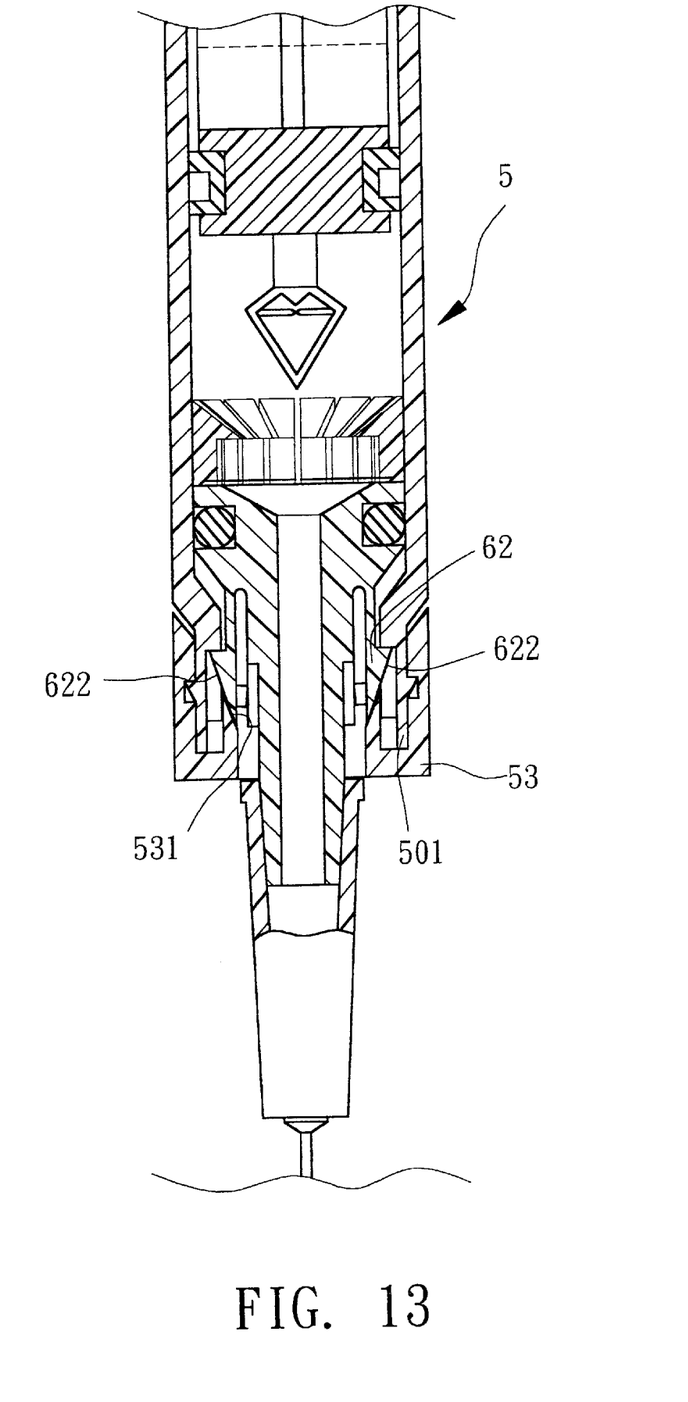
FIG. 13 is partially side cross-sectional view of a third embodiment of the syringe in accordance with the present invention.
Figure 14:
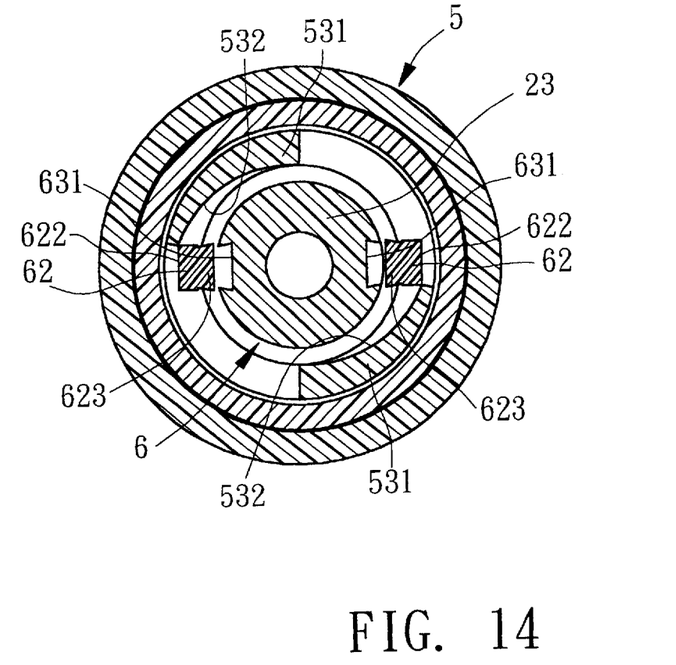
FIG. 14 is a top operational cross-sectional view of the syringe in FIG. 13.
Figure 15:
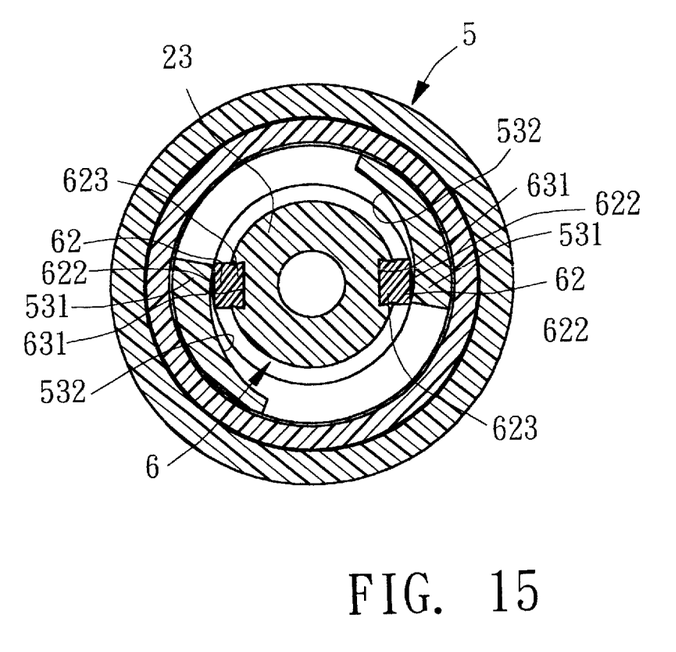
FIG. 15 is a top operational cross-sectional view of the syringe in FIG. 13.

With reference to FIGS. 13–15, it is a third embodiment of the syringe in accordance with the present invention. Each locking member (62) includes a dovetail flange (623) extending from the locking member (62) toward the needle hub (23) and a guiding side (622) formed opposite to the dovetail flange (623) under the first hook of the locking member (62). Two dovetail grooves (631) are diametrically defined in the needle hub (23) and each aligns with a corresponding one of the two dovetail flanges (623). An end cap (53) is pivotally mounted to the first end (501) of the hollow barrel (5). The end cap (53) includes two pushing blocks (531) diametrically extending from a bottom of the end cap (53). Each pushing block (531) forms a guiding side (532) facing the locking member (62). The pushing block (531) pushes the locking member (62) to make the dovetail flange (623) fixedly received in the dovetail groove (631) when the end cap (53) is rotated after the plunger (55) securely connected to the snapping device (6). Consequently, the snapping device (6) and the needle hub (23) with the needle can be pulled into the hollow barrel (5) to achieve the objective of the syringe in accordance with the present invention.

Although the invention has been explained in relation to its preferred embodiment, it is to be understood that many other possible modifications and variations can be made without departing from the spirit and scope of the invention as hereinafter claimed.

What is claimed is:

1. A syringe with a snapping device for backward pulling the needle into the syringe after syringing, the syringe comprising:

a hollow barrel having an inner periphery, an outer periphery, a front end and a flange extending from the inner periphery of the hollow barrel near the first end of the hollow barrel;

a plunger partially and movably received in the hollow barrel, the plunger including a front end toward the first end of the hollow barrel and abutting the inner periphery of the hollow barrel, and a connector centrally extending from the front end of the plunger toward the first end of the hollow barrel; and a snapping device slidably received in the hollow barrel and selectively connected to the connector of the plunger, the snapping device including:

a body slidably received in the hollow barrel and selectively engaged to the connector of the plunger;

an annular protrusion extending from an outer periphery of the body;

two locking member downward extending from the annular protrusion and diametrically corresponding to each other, each locking member having a first hook formed on a middle portion of the locking member and extending toward the inner periphery of the hollow barrel to engage to the hollow barrel, a hollow stub centrally and longitudinally extending from the body, an annular slit defined in the hollow stub, a second hook extending from the locking member opposite to the first hook and selectively engaged to the annular slit of the hollow stub and a pusher extending through the hollow barrel such that the first hook is detached from the hollow barrel when the pusher is inward compressed.

2. The syringe as claimed in claim 1, wherein the hollow barrel comprises two gaps defined in the flange of the hollow barrel, the two gaps diametrically corresponding to each other, and two slots longitudinally defined in the first end of the hollow barrel, each slot aligning with a corresponding one of the two gaps, the first hook selectively engage to a bottom of the slot and the pusher extending through the hollow barrel via the slot.

3. The syringe as claimed in claim 1 further comprising an end cap attached to the first end of the hollow barrel, the end cap including two stubs upward extending from a bottom of the end cap and each aligning with a corresponding one of the two locking member, a guiding side formed on a free end of each of the two stubs for pushing the locking member.

4. The syringe as claimed in claim 1 further comprising an end cap pivotally mounted on the first end of the hollow barrel, the end cap including two pushing block diametrically extending from a bottom of the end cap, each pushing block forming a guiding side facing the locking member for pushing the locking member.

5. The syringe as claimed in claim 1, wherein the snapping device comprises a connecting portion formed on a top of the body, the connecting portion including multiple claws each radially extending from the top of the body, the claw including a resilient portion connecting to the body and a hook formed on a free end of the claw, a concavity centrally defined in the in the top of the body within the claws, and the plunger comprises a connector centrally extending from the front end of the plunger toward the first end of the hollow barrel and selectively engaged to the snapping device, the connector including:

a shaft centrally and perpendicularly extending from the front end of the plunger;

two wing plates obliquely extending from a free end of the shaft toward the inner periphery of the hollow barrel;

two resilient plates respectively extending from a corresponding one of the free ends of the two wing plates, each resilient plate having a free end connected to each other such that the two wing plates and the two resilient plates forming a rhombus.

6. The syringe as claimed in claim 3, wherein the snapping device comprises a connecting portion formed on a top of the body, the connecting portion including multiple claws each radially extending from the top of the body, the claw including a resilient portion connecting to the body and a hook formed on a free end of the claw, a concavity centrally defined in the in the top of the body within the claws, and the plunger comprises a connector centrally extending from the front end of the plunger toward the first end of the hollow barrel and selectively engaged to the snapping device, the connector including:

a shaft centrally and perpendicularly extending from the front end of the plunger;

two wing plates obliquely extending from a free end of the shaft toward the inner periphery of the hollow barrel;

two resilient plates respectively extending from a corresponding one of the free ends of the two wing plates, each resilient plate having a free end connected to each other such that the two wing plates and the two resilient plates forming a rhombus.

7. The syringe as claimed in claim 4, wherein the snapping device comprises a connecting portion formed on a top of the body, the connecting portion including multiple claws each radially extending from the top of the body, the claw including a resilient portion connecting to the body and a hook formed on a free end of the claw, a concavity centrally defined in the in the top of the body within the claws, and the plunger comprises a connector centrally extending from the front end of the plunger toward the first end of the hollow barrel and selectively engaged to the snapping device, the connector including:

a shaft centrally and perpendicularly extending from the front end of the plunger;

two wing plates obliquely extending from a free end of the shaft toward the inner periphery of the hollow barrel;

two resilient plates respectively extending from a corresponding one of the free ends of the two wing plates, each resilient plate having a free end connected to each other such that the two wing plates and the two resilient plates forming a rhombus.

8. The syringe as claimed in claim 6, wherein the second hook is formed as a dovetail flange and two dovetail grooves are diametrically defined in the needle hub to selectively receive the dovetail flange of the locking member.

9. The syringe as claimed in claim 7, wherein the second hook is formed as a dovetail flange and two dovetail grooves are diametrically defined in the needle hub to selectively receive the dovetail flange of the locking member.

* * * * *